(12) United States Patent
Kravtchenko et al.

(10) Patent No.: US 7,651,534 B2
(45) Date of Patent: Jan. 26, 2010

(54) DIRECT DYE COMPOSITION COMPRISING AT LEAST ONE INSOLUBLE OXYGENATED COMPOUND, AND PROCESSES USING THIS COMPOSITION

(75) Inventors: Sylvain Kravtchenko, Shanghai (CN); Claude Dubief, Le Chesnay (FR)

(73) Assignee: L'Oreal SA, Paris (FR)

( * ) Notice: Subject to any disclaimer, the term of this patent is extended or adjusted under 35 U.S.C. 154(b) by 85 days.

(21) Appl. No.: 11/509,010

(22) Filed: Aug. 24, 2006

(65) Prior Publication Data

US 2007/0044251 A1 Mar. 1, 2007

(30) Foreign Application Priority Data

Aug. 25, 2005 (FR) .................................... 05 08755

(51) Int. Cl.
*A61Q 5/10* (2006.01)
(52) U.S. Cl. ...................... 8/405; 8/406; 8/407; 8/426; 8/435; 8/461; 8/552; 8/580
(58) Field of Classification Search ............ 8/405, 8/406, 407, 426, 435, 461, 552, 557, 580
See application file for complete search history.

(56) References Cited

U.S. PATENT DOCUMENTS

| | | | |
|---|---|---|---|
| 3,193,464 A | 7/1965 | Edman et al. | |
| 4,003,699 A | 1/1977 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,766,576 A | 6/1998 | Löwe et al. | |
| 5,865,853 A | 2/1999 | Schmitt et al. | |
| 6,099,592 A | 8/2000 | Vidal et al. | |
| 6,238,653 B1 | 5/2001 | Narasimhan et al. | |
| 6,254,647 B1 | 7/2001 | Fröhling | |
| 6,277,154 B1 | 8/2001 | Lorenz | |
| 6,284,003 B1 | 9/2001 | Rose et al. | |
| 6,312,674 B1 | 11/2001 | Maubru et al. | |
| 6,540,791 B1 | 4/2003 | Dias | |
| 6,730,789 B1 | 5/2004 | Birault et al. | |
| 6,824,570 B2 | 11/2004 | Vidal et al. | |
| 6,881,230 B2 | 4/2005 | Vidal | |
| 6,884,265 B2 | 4/2005 | Vidal et al. | |
| 6,884,267 B2 | 4/2005 | Vidal et al. | |
| 6,893,471 B2 | 5/2005 | Vidal | |
| 7,001,436 B2 | 2/2006 | Vidal et al. | |
| 7,022,143 B2 | 4/2006 | Vidal et al. | |
| 7,060,110 B2 | 6/2006 | Vidal et al. | |
| 7,077,873 B2 | 7/2006 | David et al. | |
| 7,217,298 B2 | 5/2007 | Legrand et al. | |
| 7,261,743 B2 | 8/2007 | Plos et al. | |
| 2002/0046431 A1* | 4/2002 | Laurent et al. ................. | 8/405 |
| 2003/0084516 A9 | 5/2003 | Kravtchenko et al. | |
| 2003/0106169 A1* | 6/2003 | Vidal et al. ..................... | 8/405 |
| 2004/0200009 A1 | 10/2004 | Vidal | |
| 2005/0081311 A1 | 4/2005 | Schmenger et al. | |
| 2005/0232953 A1 | 10/2005 | Barnikol et al. | |

FOREIGN PATENT DOCUMENTS

| | | |
|---|---|---|
| DE | 0 709 932 | 8/1941 |
| DE | 23 59 399 | 6/1975 |
| DE | 24 32 614 | 1/1976 |
| DE | 38 43 892 | 6/1990 |
| DE | 41 33 957 | 4/1993 |
| DE | 195 43 988 | 5/1997 |
| EP | 0 714 954 | 6/1996 |
| EP | 0 715 842 | 6/1996 |
| EP | 0 770 375 | 5/1997 |
| EP | 0 823 250 | 2/1998 |
| EP | 1 048 289 | 11/2000 |
| EP | 1 438 951 | 7/2004 |
| FR | 2 733 749 | 11/1996 |
| FR | 2 801 308 | 5/2001 |
| FR | 2 807 650 | 10/2001 |
| FR | 2 822 693 | 10/2002 |
| FR | 2 822 694 | 10/2002 |
| FR | 2 822 696 | 10/2002 |
| FR | 2 822 698 | 10/2002 |
| FR | 2 825 625 | 12/2002 |
| FR | 2 825 702 | 12/2002 |
| FR | 2 829 926 | 3/2003 |
| FR | 2 844 269 | 3/2004 |
| GB | 1 026 978 | 4/1966 |
| GB | 1 153 196 | 5/1969 |
| JP | 53-95693 | 8/1978 |
| JP | 55-22638 | 2/1980 |
| JP | 02-19576 | 1/1990 |
| JP | 05-163124 | 6/1993 |
| JP | 2004-26703 | 1/2004 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |

(Continued)

OTHER PUBLICATIONS

Copending U.S. Appl. No. 11/509,023, filed Aug. 24, 2006.

(Continued)

*Primary Examiner*—Eisa B Elhilo
(74) *Attorney, Agent, or Firm*—Finnegan, Henderson, Farabow, Garrett & Dunner, LLP

(57) ABSTRACT

Disclosed herein is a composition for the non-oxidizing aqueous direct dyeing of keratin materials, for example, human keratin fibers, such as the hair, comprising, in a cosmetically acceptable medium: (a) at least one water-soluble direct dye, and (b) at least one water-insoluble non-coloring oxygenated organic compound, present in an amount of at least 30% by weight relative to the total weight of the composition. Also disclosed herein is a process for direct dyeing keratin fibers comprising applying said composition to the fibers.

19 Claims, No Drawings

FOREIGN PATENT DOCUMENTS

| WO | WO 02/078660 | 10/2002 |
| WO | WO 02/100369 | 12/2002 |
| WO | WO 02/100834 | 12/2002 |
| WO | WO 03/105797 | 12/2003 |
| WO | WO 2005/074871 | 8/2005 |
| WO | WO 2005/074873 | 8/2005 |

OTHER PUBLICATIONS

Copending U.S. Appl. No. 11/509,022, filed Aug. 24, 2006.
French Search Report for FR 05/08753 (copending U.S. Appl. No. 11/509,023), dated May 12, 2006.
French Search Report for FR 05/08754 (copending U.S. Appl. No. 11/509,022), dated May 12, 2006.
French Search Report for FR 05/08755 (present application), dated May 12, 2006.
"The Science of Hair Care", Edited by Charles Zviak, Marcel Dekker Inc., 1986.
English language abstract of DE 24 32 614, Jan. 22, 1976.
English language abstract of EP 0 770 375, May 2, 1997.
English language abstract of EP 1 048 289, Nov. 2, 2000.
English language abstract of JP 53-095693, Aug. 22, 1978.
English language abstract of JP 55-022638, Feb. 18, 1980.
English language abstract of JP 02-019576, Jan. 23, 1990.
English language abstract of JP 05-163124, Jun. 29, 1993.
English language abstract of JP 2004-026703, Jan. 29, 2004.
English language abstract of WO 2005/074871, Aug. 18, 2005.
English language abstract of WO 2005/074873, Aug. 18, 2005.
Office Action mailed Dec. 23, 2008, in co-pending U.S. Appl. No. 11/509,023.
Office Action mailed Feb. 25, 2009, in co-pending U.S. Appl. No. 11/509,022.
Office Action mailed Jul. 2, 2008, in co-pending U.S. Appl. No. 11/509,022.
Office Action mailed Jun. 19, 2008, in co-pending U.S. Appl. No. 11/509,023.

* cited by examiner

DIRECT DYE COMPOSITION COMPRISING AT LEAST ONE INSOLUBLE OXYGENATED COMPOUND, AND PROCESSES USING THIS COMPOSITION

This application claims benefit of priority under 35 U.S.C. § 119 to French Patent Application No. FR 05 08755, filed Aug. 25, 2005, the contents of which are also incorporated herein by reference.

Disclosed herein are compositions for the non-oxidizing aqueous direct dyeing of keratin materials, for example, human keratin fibers such as the hair, comprising at least one water-insoluble compound. Also disclosed herein is a process for the direct dyeing of keratin fibers comprising applying such a composition to the fibers.

It is known practice to dye keratin fibers, for example, human hair, with dye compositions comprising oxidation dye precursors, which are generally known as oxidation bases, such as ortho- or para-phenylenediamines, ortho- or para-aminophenols, and heterocyclic compounds. These oxidation bases are colorless or weakly colored compounds, which, when combined with oxidizing products, give rise to colored compounds by a process of oxidative condensation.

It is also known that the shades obtained with these oxidation bases may be varied by combining them with couplers or coloration modifiers, the latter being chosen, for example, from aromatic meta-diamines, meta-aminophenols, meta-diphenols, and heterocyclic compounds, such as indole compounds.

The variety of molecules available as oxidation bases and couplers allows a rich palette of colors to be obtained.

The "permanent" dyeing obtained by means of these oxidation dyes ideally satisfies at least one of a number of requirements. For example, the dyeing ideally does not have any toxicological drawbacks, allows shades to be obtained in the desired intensity, shows good fastness with respect to external agents, such as light, bad weather, washing, permanent waving, perspiration, and/or rubbing, allows gray hair to be covered, and is as unselective as possible, i.e., allows the smallest possible coloration differences along the same keratin fiber, which is generally differently sensitized (i.e., damaged) between its end and its root.

It is also known practice to dye keratin fibers by direct or semi-permanent dyeing. The process conventionally used in direct dyeing comprises applying to the keratin fibers direct dyes, which are colored and coloring molecules that have affinity for the fibers, leaving the dyes to act in order to allow the colored molecules to penetrate, by diffusion, into the hair, and then rinsing the fibers.

In contrast with oxidation dye compositions, direct or semi-permanent dye compositions may be used without the obligatory presence of an oxidizing agent. In addition, these direct dyeing operations may be performed repeatedly without degrading the keratin fiber.

It is known practice, for example, to use direct dyes of the nitrobenzene, anthraquinone, nitropyridine, azo, xanthene, acridine, azine, and triarylmethane dyes.

The leave-on time of a direct dye composition conventionally ranges from 15 to 45 minutes, depending on the nature of the fiber (sensitized or non-sensitized) and the nature of the dye used. A great deal of research has been conducted on reducing the leave-on time of dye compositions without, however, increasing the concentration of the constituents, while at the same time maintaining a good level of dyeing, i.e., good dyeing power and good fastness of the color with respect to external agents and over time.

Thus, it would be useful to provide direct dye compositions that are improved in terms of efficacy and speed of reaction and/or of penetration of the dye into the fiber, while at the same time maintaining good harmlessness, good resistance, and good selectivity, the latter resulting from the difference in color uptake between different parts of a hair or of a head of hair.

The present inventors have discovered that the use of compositions for dyeing keratin fibers, for example, human keratin fibers such as the hair, comprising at least one water-soluble direct dye and at least one water-insoluble compound in a certain amount provides at least one of the improvements mentioned above.

These compositions may have the advantage of being less harmful to the hair, shortening the leave-on time of the composition on the fibers to be dyed, allowing uniform, resistant tints to be obtained.

In addition, these compositions may have a good toxicological profile.

Also disclosed herein is a direct dyeing process comprising applying a composition of the present disclosure to keratin fibers.

Other characteristics, aspects, subjects, and advantages will be understood more clearly upon reading the description below.

Disclosed herein is thus a composition for the non-oxidizing aqueous direct dyeing of keratin materials, for example, human keratin fibers such as the hair, comprising, in a cosmetically acceptable medium:
 (a) at least one water-soluble direct dye, and
 (b) at least one water-insoluble non-coloring oxygenated organic compound, present in an amount of at least 30% by weight relative to the total weight of the dye composition.

As used herein, the term "oxygenated organic compound" means any organic compound comprising at least one oxygen atom in its elemental molecular structure.

As used herein, the term "insoluble non-coloring oxygenated organic compound" means any oxygenated organic compound that is incapable of dyeing the hair using the compositions of the present disclosure and that has a solubility in water at room temperature (25° C.) of less than 0.5% by weight.

As used herein, the term "non-oxidizing composition" means any composition not containing a peroxygenated organic compound such as hydrogen peroxide, persulfates, perborates, and/or peracids.

The dye composition in accordance with the present disclosure comprises at least one water-soluble direct dye conventionally used in direct dyeing and of any polarity.

As used herein, the term "water-soluble dye" means a dye whose solubility at 25° C. and at pH 7 in water and/or in a mixture of water (85% by weight) and hexylene glycol (15% by weight) is greater than or equal to 0.1%.

The direct dyes useful in accordance with the present disclosure may be chosen from neutral, acidic, or cationic nitrobenzene dyes; neutral, acidic, or cationic azo direct dyes; neutral, acidic, or cationic quinone, for instance, anthraquinone, direct dyes; azine direct dyes; triarylmethane direct dyes; indoamine direct dyes; and natural direct dyes.

Non-limiting examples of benzene-based direct dyes that may be used herein include:
 1,4-diamino-2-nitrobenzene,
 1-amino-2-nitro-4-β-hydroxyethylaminobenzene,
 1-amino-2-nitro-4-bis(β-hydroxyethyl)aminobenzene,
 1,4-bis(β-hydroxyethylamino)-2-nitrobenzene, 1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene, and
1-hydroxy-4-β-hydroxyethylamino-3-nitrobenzene.

Suitable azo direct dyes may be chosen from, but not limited to, the cationic azo dyes described in International Patent Application Publication Nos. WO 95/15144, WO 95/01772, WO 02/078 660, WO 02/100 834, and WO 02/100 369, European Patent Application No. 0 714 954, and French Patent Application Nos. 2 822 696, 2 825 702, 2 825 625, 2 822 698, 2 822 693, 2 822 694, 2 829 926, 2 807 650, and 2 844 269, which are incorporated herein by reference in their entireties.

Examples of such azo compounds include, but are not limited to:
  1,3-dimethyl-2-[[4-(dimethylamino)phenyl]azo]-1H-imidazolium chloride,
  1,3-dimethyl-2-[(4-aminophenyl)azo]-1H-imidazolium chloride, and
  1-methyl-4-[(methylphenylhydrazono)methyl]pyridinium methyl sulfate.

Further non-limiting examples of suitable azo direct dyes include the following dyes, described in the Color Index International, 3rd edition:
  Acid Yellow 9,
  Acid Black 1,
  Basic Red 22,
  Basic Red 76,
  Basic Yellow 57,
  Basic Brown 16,
  Acid Yellow 36,
  Acid Orange 7,
  Acid Red 33,
  Acid Red 35,
  Basic Brown 17,
  Acid Yellow 23, and
  Acid Orange 24.
  1-(4'-aminodiphenylazo)-2-methyl-4-bis(β-hydroxyethyl)aminobenzene and 4-hydroxy-3-(2-methoxyphenylazo)-1-naphthalenesulfonic acid are also suitable for use as azo direct dyes.

Quinone direct dyes may be chosen, for example, from:
  Acid Violet 43,
  Acid Blue 62,
  Basic Blue 22,
  Basic Blue 99, and also
  1-N-methylmorpholiniumpropylamino-4-hydroxyanthraquinone,
  1-aminopropylamino-4-methylaminoanthraquinone,
  1-aminopropylaminoanthraquinone,
  5-β-hydroxyethyl-1,4-diaminoanthraquinone,
  2-aminoethylaminoanthraquinone, and
  1,4-bis(β,γ-dihydroxypropylamino)anthraquinone.

Non-limiting examples of azine dyes include:
  Basic Blue 17, and
  Basic Red 2.

Suitable triarylmethane dyes may include, for example:
  Basic Green 1,
  Acid blue 9,
  Basic Violet 3,
  Basic Violet 14,
  Basic Blue 7,
  Acid Violet 49,
  Basic Blue 26, and
  Acid Blue 7.

A non-limiting example of an indoamine dye that may be used in accordance with the present disclosure is:
  2-β-hydroxyethylamino-5-[bis(β-4'-hydroxyethyl)amino]anilino-1,4-benzoquinone.

Natural direct dyes may be chosen, for example, from carminic acid, kermesic acid, purpurogallin, protocatechaldehyde, isatin, curcumin, spinulosin, and apigenidin. It is also possible to use extracts or decoctions containing these natural dyes, for example, henna-based poultices and extracts.

The at least one direct dye may be present in the dye composition in an amount ranging from 0.001% to 20% by weight relative to the total weight of the dye composition, for example, from 0.005% to 10% by weight.

The insoluble oxygenated organic compounds according to the present disclosure may be chosen, for example, from polyamides 6, 66, and 11, polyesters, polyurethanes, polycyanoacrylates, polymethyl methacrylates, polycarbonates, Teflon (polytetrafluoroethylene), and silicone resins and elastomers.

Non-limiting examples of insoluble oxygenated organic compounds include fatty alcohols comprising from 8 to 40 carbon atoms, fatty acid esters and ethers, and fatty alcohol esters and ethers, the fatty chains of these fatty acids or fatty alcohols comprising from 8 to 40 carbon atoms and being optionally hydroxylated. Examples of such compounds may include: ethylene glycol monostearate and distearate, pentaerythrityl monooleate, sorbitan tristearate, glyceryl dioleate, fatty esters, amides and ethers of ethylene glycol, amides and ethers of propylene glycol, distearyl ether, stearyl alcohol, behenyl alcohol, and cetylstearyl alcohol.

The at least one water-insoluble oxygenated organic compound may be present in the dye composition in an amount greater than 30% by weight relative to the total weight of the dye composition, for example, ranging from 30% to 90% by weight, or from 30% to 60% by weight.

Thus, in at least one embodiment, when the at least one water-insoluble compound according to the present disclosure is solid, the composition is in the form of a suspension. When the at least one water-insoluble compound according to the present disclosure is in liquid form, for example, in the form of an organic phase that is insoluble in the aqueous phase, the composition may be in a form chosen from emulsions and dispersions.

The suitable dyeing medium, also known as the dye support, is a cosmetic medium generally chosen from water and mixtures of water and at least one organic solvent. Examples of suitable organic solvents include, but are not limited to, $C_1$-$C_4$ lower alkanols, such as ethanol and isopropanol; polyols and polyol ethers, for instance 2-butoxyethanol, propylene glycol, glycerol, polyol monoethers such as propylene glycol monomethyl ether, diethylene glycol monoethyl ether, and monomethyl ether; and aromatic alcohols, for instance benzyl alcohol and phenoxyethanol; and mixtures thereof.

The composition according to the present disclosure may comprise water in an amount ranging from 0.1% to 69.995%, for example, from 10% to 68%, from 20% to 65%, or from 30% to 60% by weight, relative to the total weight of the dye composition.

The at least one organic solvent may be present in the composition in an amount ranging from 1% to 40% by weight, for example, from 5% to 30% by weight, relative to the total weight of the dye composition.

The dye composition in accordance with the present disclosure may also comprise at least one adjuvant conventionally used in hair dye compositions, such as anionic, cationic, nonionic, amphoteric, or zwitterionic surfactants and mixtures thereof; anionic, cationic, nonionic, amphoteric, or zwitterionic polymers and mixtures thereof; mineral and organic thickeners, such as anionic, cationic, nonionic, and amphoteric associative thickeners; antioxidants; penetrants; sequestrants; fragrances; buffers; dispersants; conditioning agents, for instance volatile or non-volatile, modified or unmodified silicones; film-forming agents; ceramides; preserving agents; and opacifiers.

The at least one adjuvant may be present in the dye composition in an amount, for each of them, ranging from 0.01% to 20% by weight relative to the total weight of the dye composition.

It is to be understood that a person skilled in the art will take care to select the at least one optional additional compound such that the advantageous properties intrinsically associated with the dye composition in accordance with the present disclosure are not, or are not substantially, adversely affected by the envisaged addition.

The pH of the dye composition in accordance with the present disclosure may range from 3 to 12, for example, from 5 to 11, or from 6 to 8.5. The pH may be adjusted to the desired value by means of acidifying or basifying agents usually used for dyeing keratin fibers, or alternatively, using standard buffer systems.

Non-limiting examples of acidifying agents include mineral and organic acids such as hydrochloric acid, orthophosphoric acid, sulfuric acid, carboxylic acids, for instance acetic acid, tartaric acid, citric acid, and lactic acid, and sulfonic acids.

Suitable basifying agents include, for example, aqueous ammonia, alkaline carbonates, alkanolamines such as monoethanolamine, diethanolamine, triethanolamine, and derivatives thereof, sodium hydroxide, potassium hydroxide, and compounds of formula (II):

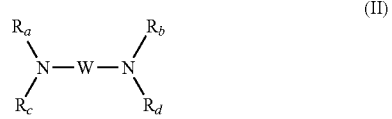

wherein:
 W is a propylene residue optionally substituted with at least one entity chosen from hydroxyl groups and $C_1$-$C_4$ alkyl radicals; and
 $R_a$, $R_b$, $R_c$, and $R_d$, which may be identical or different, are chosen from hydrogen, $C_1$-$C_4$ alkyl radicals, and $C_1$-$C_4$ hydroxyalkyl radicals.

In at least one embodiment, the composition according to the present disclosure may result from the extemporaneous mixing of two or more compositions. For example, the composition may be obtained by mixing a dye support comprising the at least one water-insoluble oxygenated organic compound with an aqueous composition comprising the at least one direct dye.

The dye composition according to the present disclosure may be in various forms, such as liquids, creams, and gels, or in any other form that is suitable for dyeing keratin fibers, for example, human hair. This is likewise the case for the compositions which, after mixing together, lead to the composition according to the present disclosure, with the proviso that at least one of them is an aqueous solution.

Also disclosed herein is a process for direct dyeing of keratin fibers comprising applying a composition according to the present disclosure to the fibers, and then rinsing the fibers.

In at least one embodiment, the dye composition according to the present disclosure is applied to the keratin fibers and left on the fibers for a time period ranging from 3 minutes to 1 hour, for example, from 15 minutes to 45 minutes, followed by rinsing the fibers.

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the present disclosure are approximations, unless otherwise indicated the numerical values set forth in the specific examples are reported as precisely as possible. Any numerical value, however, inherently contain certain errors necessarily resulting from the standard deviation found in their respective testing measurements.

By way of non-limiting illustration, concrete examples of certain embodiments of the present disclosure are given below.

EXAMPLES

The following compositions were prepared:

| | |
|---|---|
| Distearyl ether | 34 g |
| Sodium lauryl sulfate | 2 g |
| Brij 700 | 1 g |
| Ammonium acryloyldimethyltaurate/Steareth 20 methacrylate crosspolymer | 2 g |
| Water-soluble direct dye** | 0.15 g |
| 2-Amino-2-methyl-1-propanol | qs pH 8.5 |
| Demineralized water | qs 100 g |

**The water-soluble direct dye was chosen as follows for Examples 1-4:
Example 1: water-soluble direct dye Basic Red 51
Example 2: water-soluble direct dye Acid Red 35
Example 3: water-soluble direct dye Carminic acid
Example 4: 1-β-hydroxyethylamino-2-nitro-4-aminobenzene The compositions of the four examples were applied for 30 minutes at room temperature to hair comprising 90% white hairs. After rinsing and drying, the hair was dyed an auburn color that was stronger than if the distearyl ether was replaced with a water-soluble non-coloring compound such as ethanol.

Similar results may be obtained by replacing the distearyl ether weight-for-by weight with Nylon-6 powder sold by Induchem under the name Inducos.

What is claimed is:

1. A composition for the non-oxidizing aqueous direct dyeing of keratin materials, comprising, in a cosmetically acceptable medium:
   (a) at least one water-soluble direct dye,
   (b) at least one water-insoluble non-coloring oxygenated organic compound, present in an amount of at least 30% by weight relative to the total weight of the composition,
   wherein the at least one water insoluble non-coloring oxygenated organic compound is chosen from:
   polyamides 6, 66, and 11, polyesters, polyurethanes, polycyanoacrylates, polymethyl methacrylates, polycarbonates, polytetrafluoroethylene, and silicone resins and elastomers, and
   fatty alcohols comprising a $C_8$-$C_{40}$ fatty chain, fatty acid ester and ethers, and fatty alcohol esters and ethers, the fatty chains of these fatty acids and fatty alcohols comprising from 8 to 40 carbon atoms
   wherein said composition does not include a peroxygenated organic compound.

2. The composition according to claim 1, wherein the at least one direct dye is chosen from neutral, acidic, or cationic nitrobenzene dyes; neutral, acidic, or cationic azo direct dyes; neutral, acidic, or cationic quinone and anthraquinone direct dyes; azine direct dyes; triarylmethane direct dyes; indoamine direct dyes; and natural direct dyes.

3. The composition according to claim 2, wherein the at least one direct dye is chosen from:
1,4-diamino-2-nitrobenzene,
1-amino-2-nitro-4-β-hydroxyethylaminobenzene,
1-amino-2-nitro-4-bis(β-hydroxyethyl)aminobenzene,
1,4-bis(β-hydroxyethylamino)-2-nitrobenzene,
1-β-hydroxyethylamino-2-nitro-4-bis(β-hydroxyethylamino)benzene,
1-β-hydroxyethylamino-2-nitro-4-aminobenzene,
1-β-hydroxyethylamino-2-nitro-4-(ethyl)(β-hydroxyethyl)aminobenzene,
1-amino-3-methyl-4-β-hydroxyethylamino-6-nitrobenzene,
1-amino-2-nitro-4-β-hydroxyethylamino-5-chlorobenzene,
1,2-diamino-4-nitrobenzene,
1-amino-2-β-hydroxyethylamino-5-nitrobenzene,
1,2-bis(β-hydroxyethylamino)-4-nitrobenzene,
1-amino-2-tris(hydroxymethyl)methylamino-5-nitrobenzene,
1-hydroxy-2-amino-5-nitrobenzene,
1-hydroxy-2-amino-4-nitrobenzene,
1-hydroxy-3-nitro-4-aminobenzene,
1-β-hydroxyethyloxy-2-β-hydroxyethylamino-5-nitrobenzene,
1-methoxy-2-β-hydroxyethylamino-5-nitrobenzene,
1-β-hydroxyethyloxy-3-methylamino-4-nitrobenzene,
1-β,γ-dihydroxypropyloxy-3-methylamino-4-nitrobenzene,
1-β-hydroxyethylamino-4-β,γ-dihydroxypropyloxy-2-nitrobenzene,
1-β,γ-dihydroxypropylamino-4-trifluoromethyl-2-nitrobenzene,
1-β-hydroxyethylamino-4-trifluoromethyl-2-nitrobenzene,
1-β-hydroxyethylamino-3-methyl-2-nitrobenzene,
1-β-aminoethylamino-5-methoxy-2-nitrobenzene,
1-hydroxy-2-chloro-6-ethylamino-4-nitrobenzene,
1-hydroxy-2-chloro-6-amino-4-nitrobenzene,
1-hydroxy-6-bis(β-hydroxyethyl)amino-3-nitrobenzene,
1-β-hydroxyethylamino-2-nitrobenzene,
1-hydroxy-4-β-hydroxyethylamino-3-nitrobenzene,
1,3-dimethyl-2-[[4-(dimethylamino)phenyl]azo]-1H-imidazolium chloride,
1,3-dimethyl-2-[(4-aminophenyl)azo]-1H-imidazolium chloride,
1-methyl-4-[(methylphenylhydrazono)methyl]pyridinium methyl sulfate,
Acid Yellow 9,
Acid Black 1,
Basic Red 22,
Basic Red 76,
Basic Yellow 57,
Basic Brown 16,
Acid Yellow 36,
Acid Orange 7,
Acid Red 33,
Acid Red 35,
Basic Brown 17,
Acid Yellow 23,
Acid Orange 24,
1-(4'-aminodiphenylazo)-2-methyl-4-bis(β-hydroxyethyl)aminobenzene 4-hydroxy-3-(2-methoxyphenylazo)-1-naphthalenesulfonic acid,
Acid Violet 43,
Acid Blue 62,
Basic Blue 22,
Basic Blue 99,
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminoethylaminoanthraquinone,
1,4-bis(β,γ-dihydroxypropylamino)anthraquinone,
Basic Blue 17,
Basic Red 2,
Basic Green 1,
Acid blue 9,
Basic Violet 3, Basic Violet 14,
Basic Blue 7,
Acid Violet 49,
Basic Blue 26,
Acid Blue 7,
2-β-hydroxyethylamino-5-[bis(β-4'-hydroxyethyl)amino]anilino-1,4-benzoquinone,
carminic acid,
kermesic acid,
purpurogallin,
protocatechaldehyde,
isatin,
curcumin,
spinulosin, and
apigenidin.

4. The composition according to claim 1, wherein the at least one water-soluble direct dye is present in the composition in an amount ranging from 0.001% to 20% by weight relative to the total weight of the composition.

5. The composition according to claim 4, wherein the at least one water-soluble direct dye is present in an amount ranging from 0.005% to 10% by weight relative to the total weight of the composition.

6. The composition according to claim 1, wherein the at least one water-insoluble non-coloring oxygenated organic compound is present in the composition in an amount ranging from 30% to 90% by weight relative to the total weight of the composition.

7. The composition according to claim 6, wherein the at least one water-insoluble non-coloring oxygenated organic compound is present in the composition in an amount ranging from 30% to 60% by weight relative to the total weight of the composition.

8. The composition of claim 1, further comprising water in an amount ranging from 0.1% to 69.995% by weight relative to the total weight of the composition.

9. The composition according to claim 8, wherein the water is present in an amount ranging from 10% to 68% by weight relative to the total weight of the composition.

10. The composition according to claim 9, wherein the water is present in an amount ranging from 20% to 65% by weight relative to the total weight of the composition.

11. The composition according to claim 10, wherein the water is present in an amount ranging from 30% to 60% by weight relative to the total weight of the composition.

12. The composition according to claim 1, further comprising at least one hydroxylated solvent chosen from ethanol, propylene glycol, glycerol, and polyol monoethers.

13. The composition according to claim 1, further comprising at least one adjuvant chosen from anionic, cationic, nonionic, amphoteric, or zwitterionic surfactants and mixtures thereof; anionic, cationic, nonionic, amphoteric, or zwitterionic polymers and mixtures thereof; mineral and organic thickeners; antioxidants; penetrants; sequestrants; fragrances; buffers; dispersants; conditioning agents; film-forming agents; ceramides; preserving agents; and opacifiers.

14. The composition according to claim 13, wherein said mineral and organic thickeners are chosen from anionic, cationic, nonionic, and amphoteric polymeric associative thickeners.

15. The composition according to claim 13, wherein said conditioning agents are chosen from volatile or non-volatile, modified or unmodified silicones.

16. A process for dyeing keratin fibers, comprising applying a dye composition to the keratin fibers, leaving it on the fibers to act for a time period ranging from 3 minutes to 1 hour, and rinsing the fibers,
wherein the dye composition comprises, in a cosmetically acceptable medium:
(a) at least one water-soluble direct dye,
(b) at least one water-insoluble non-coloring oxygenated organic compound, present in an amount of at least 30% by weight relative to the total weight of the composition,
wherein the at least one water insoluble non-coloring oxygenated organic compound is chosen from:
polyamides 6, 66, and 11, polyesters, polyurethanes, polycyanoacrylates, polymethyl methacrylates, polycarbonates, polytetrafluoroethylene, and silicone resins and elastomers, and
fatty alcohols comprising a $C_8$-$C_{40}$ fatty chain, fatty acid ester and ethers, and fatty alcohol esters and ethers, the fatty chains of these fatty acids and fatty alcohols comprising from 8 to 40 carbon atoms
wherein said composition does not include a peroxygenated organic compound.

17. The process according to claim 16, wherein the time period ranges from 15 minutes to 45 minutes.

18. The composition according to claim 1, wherein the at least one water insoluble non-coloring oxygenated organic compound is chosen from ethylene glycol monostearate and distearate, pentaerythrityl monooleate, sorbitan tristearate, glyceryl dioleate, fatty esters, amides, and ethers of ethylene glycol, fatty esters, amides, and ethers of propylene glycol, distearyl ether, stearyl alcohol, behenyl alcohol, and cetyl-stearyl alcohol.

19. The process according to claim 16, wherein the at least one water insoluble non-coloring oxygenated organic compound is chosen from ethylene glycol monostearate and distearate, pentaerythrityl monooleate, sorbitan tristearate, glyceryl dioleate, fatty esters, amides, and ethers of ethylene glycol, fatty esters, amides, and ethers of propylene glycol, distearyl ether, stearyl alcohol, behenyl alcohol, and cetyl-stearyl alcohol.

* * * * *